United States Patent [19]

Tanaka

[11] Patent Number: 4,997,723
[45] Date of Patent: Mar. 5, 1991

[54] METAL-PORCELAIN DENTAL RESTORATIONS, DENTAL VENEERS, DENTAL BRIDGES AND METAL FOIL FOR USE THEREIN AND METHODS FOR MAKING DENTAL APPLIANCES

[75] Inventor: Asami Tanaka, Skokie, Ill.

[73] Assignee: Tanaka Dental Enterprises, Skokie, Ill.

[21] Appl. No.: 480,557

[22] Filed: Feb. 14, 1990

Related U.S. Application Data

[63] Continuation-in-part of Ser. No. 49,119, May 13, 1987, abandoned.

[51] Int. Cl.$^5$ .................. C22C 5/02; A61C 13/09
[52] U.S. Cl. .................. 428/606; 420/507; 420/508; 420/510; 420/511; 420/512; 433/207
[58] Field of Search .............. 433/207, 208, 218, 222, 433/223, 227; 428/601, 606, 670, 672; 420/508, 509, 510, 511, 512

[56] References Cited

U.S. PATENT DOCUMENTS

| | | | |
|---|---|---|---|
| 192,167 | 6/1877 | Huguenin | 29/179 |
| 418,380 | 12/1889 | Parker et al. | 433/203.1 |
| 646,764 | 4/1900 | Steele | 433/239 |
| 1,561,247 | 11/1925 | Kingsbury | 420/511 |
| 1,659,757 | 2/1928 | Aderer | 428/672 |
| 1,946,231 | 2/1934 | Nowack | 420/510 |
| 2,572,377 | 10/1951 | O'Morrow | 433/203.1 |
| 2,947,623 | 8/1960 | Lincoln | 420/508 |
| 2,980,998 | 4/1961 | Coleman et al. | 433/222.1 |
| 3,136,633 | 6/1964 | Berry | 420/508 |
| 3,340,050 | 9/1967 | Nielsen | 433/207 |
| 3,413,723 | 12/1968 | Wagner et al. | 433/207 |
| 3,666,540 | 5/1972 | Burnett | 433/207 |
| 3,716,356 | 2/1973 | Burnett | 420/508 |
| 4,132,830 | 1/1979 | Tsai | 433/207 |
| 4,218,244 | 8/1980 | Knosp | 433/207 |
| 4,392,829 | 7/1983 | Tanaka | 433/222 |
| 4,459,112 | 7/1984 | Shoher et al. | 433/218 |
| 4,486,386 | 12/1984 | Mizuhara | 428/606 |
| 4,676,751 | 6/1987 | Shoher et al. | 433/218 |
| 4,794,774 | 1/1989 | Clark et al. | 264/19 |

FOREIGN PATENT DOCUMENTS

| | | | |
|---|---|---|---|
| 8975 | 3/1980 | European Pat. Off. | 420/509 |
| 16315 | 10/1980 | European Pat. Off. | 433/222.1 |
| 48-23765 | 6/1973 | Japan | 420/511 |
| 377380 | 4/1973 | U.S.S.R. | 420/511 |

OTHER PUBLICATIONS

T. Kurobe et al., Chemical Abstracts 105:231008m, "Extension of Gold Leaf by Cyclic Impact Loading", 1986, p. 262.

*Primary Examiner*—John J. Zimmerman
*Attorney, Agent, or Firm*—Roper & Quigg

[57] ABSTRACT

A metal foil is provided for use in a metal-porcelain dental restoration, which metal foil provides improved color qualities to the finished restoration and improved bonding of the metal to the porcelain. The metal foil is made of an alloy comprising a major amount of gold, an amount of platinum or palladium, and an amount of a non-precious metal. An improved dental veneer and dental bridge can also be made using the metal foil of the invention.

11 Claims, 4 Drawing Sheets

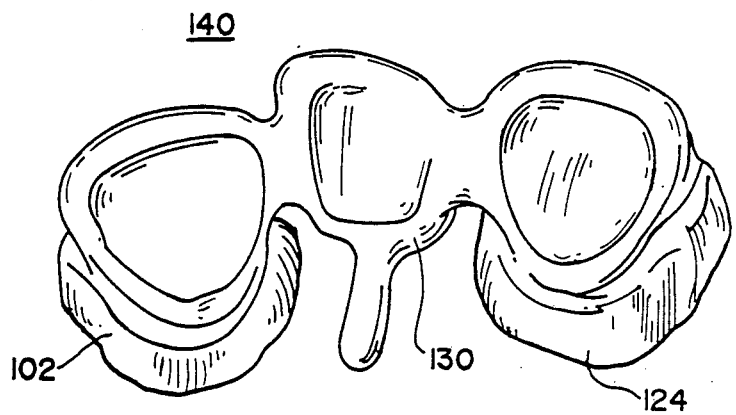
FIG. 9
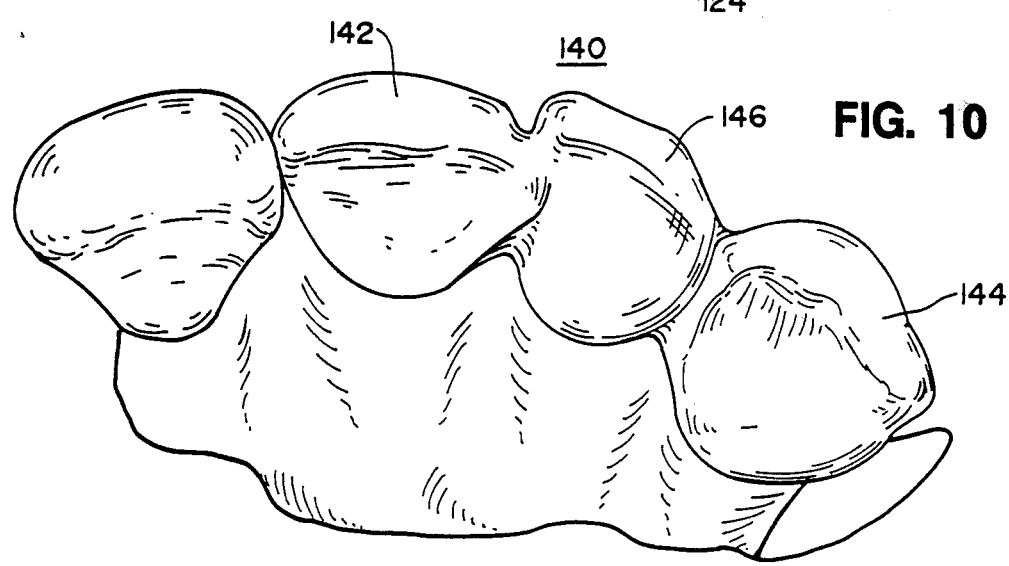
FIG. 10
FIG. 11
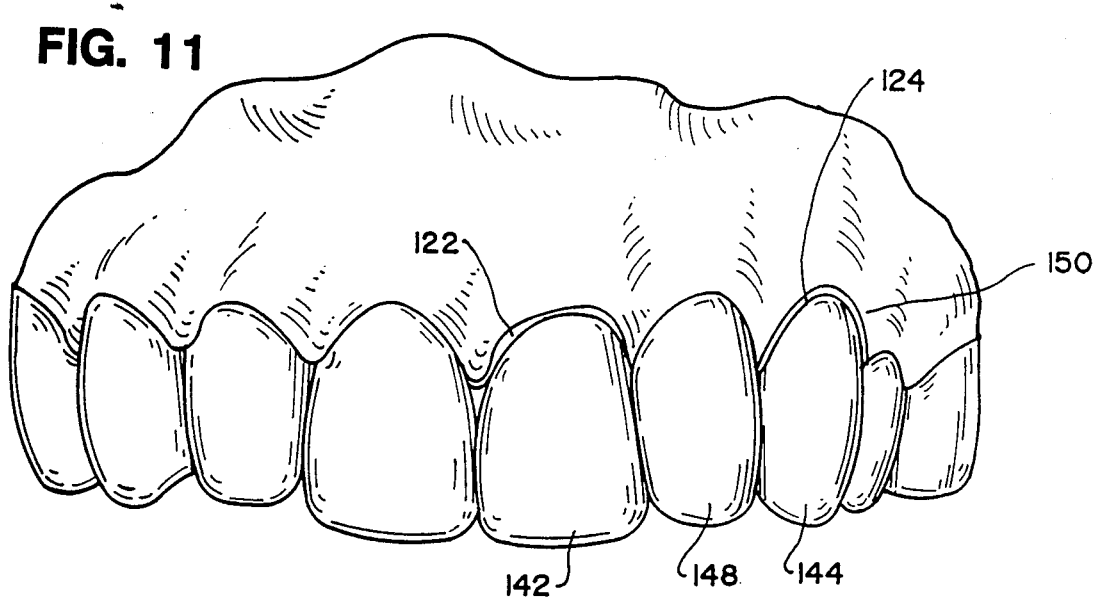

METAL-PORCELAIN DENTAL RESTORATIONS, DENTAL VENEERS, DENTAL BRIDGES AND METAL FOIL FOR USE THEREIN AND METHODS FOR MAKING DENTAL APPLIANCES

This application is a continuation-in-part of my copending application Ser. No. 049,119 filed May 13, 1987, now abandoned.

FIELD OF THE INVENTION

This invention relates to improved metal-porcelain dental restorations, improved metal-porcelain dental veneers, improved dental bridges and an improved metal foil for use in such dental applications.

BACKGROUND OF THE INVENTION

It is a goal in the art of artificial porcelain dental restorations and veneers to match as closely as possible the appearance of the patient's surrounding natural dentition. In particular it is desirable for the color of the artificial restoration or veneer to match as closely as possible the color of the adjacent teeth. As natural tooth color varies among individuals, it is necessary for the dental technician or dentist to be able to control the color to properly match the natural teeth of each individual patient.

There are many types of porcelain dental restorations. The technique used for color matching will vary depending on the type of porcelain restoration made. Modern porcelain restorations typically include porcelain bonded to an underlying metal substructure. The porcelain typically includes an opaque base layer, an intermediate layer of dentin porcelain, and an outer layer of enamel porcelain. In some cases, the metal substructure is covered with a bonding agent to promote bonding of the porcelain to the metal. The color of the completed restoration is a function of the color and opacity of the opaque, dentin, and enamel layers of the porcelain, the color of the metal substructure, and the color of the bonding agent in cases where it is used. In these restorations, the dental technician adjusts the color of the total restoration by adjusting the colors of each of the components of the restoration. Most often, the underlying metal substructure gives an unappealing grayish cast to the restoration. Attempts to hide the gray color result in a thicker and more opaque porcelain which tends to look unnatural when compared to the natural translucency of human teeth. This is particularly true in cases where very thin restorations are used.

A new type of metal porcelain restoration has been introduced as described in U.S. Pat. No. 4,392,829, issued July 12, 1983, the complete disclosure of which is incorporated herein by reference. That invention relates to a dental restoration wherein the metal substructure is a thin platinum foil having a textured surface to which porcelain is directly applied. The foil is swaged over a die of the tooth, the foil is sand blasted to texturize the surface, porcelain paste is applied directly to the textured surface of the foil, and the restoration is baked to harden the porcelain and bond it to the foil. The invention eliminates the need for the application of a bonding agent to the foil, which had previously been necessary to promote adhesion of the porcelain to the foil. The platinum foil, however, has a gray appearance which presents the same color matching problems experienced in restoration of the prior art.

Dental bridges are a kind of porcelain dental restoration designed to fill edentulous regions. Existing dental bridges suffer the same shortcomings as other dental restorations. In addition, because of the greater size, dental bridges have additional breakage problems. In particular, at the joints between the teeth on either side of the edentulous region and the edentulous region itself, the metal is thin and often breaks.

Rather than using an entire dental restoration, dental veneers are sometimes used when it is desirable to replace worn-down portions of teeth or to attempt to provide a more desirable color to a discolored tooth.

There are various types of conventional dental veneers, all are typically made entirely of porcelain without the inclusion of a metal substructure. The conventional veneers generally have three porcelain layers: an opaque base layer, an intermediate layer of dentin porcelain, and an outer layer of enamel porcelain. Typically, these veneers have a total thickness of greater than 500 microns.

These dental veneers are bonded to the patient's natural tooth by first etching the surface of the tooth to promote bonding. This etching technique is well known in the art. After etching, the porcelain dental veneer is bonded to the tooth surface using a bonding agent. The use of these all-porcelain veneers does not mask severe discoloration of the underlying tooth and is also affected by the color of the bonding material. Moreover, the veneer does not have great strength by itself. Thin veneers, which are more desirable from an aesthetic viewpoint, are easily broken when being bonded. Furthermore, in a posterior occlusal usage, the tooth must be ground extensively to allow the use of a thicker occlusal onlay or a crown. While a platinum or palladium foil could be used as the metallic base of a metal porcelain dental veneer, as with dental restorations, the gray color of the foil would prevent a natural looking veneer especially because veneers are thin.

It is known in the art that gold metal has a more esthetically pleasing color when used as a substructure in dental restorations. Gold colored alloys, however, do not have sufficient tensile strength and hardness to serve as dental restoration substructures. One attempt to provide a metallic substructure having both suitable physical properties and an esthetically pleasing color involved a bimetallic backing having a thicker layer of white colored alloy and a thinner layer of gold colored alloy, as described in U.S. Pat. No. 2,572,377 issued Oct. 23, 1951 to R. E. O'Morrow. This backing disadvantageously requires the preparation and welding together of two distinct alloy materials.

It would be desirable to have for use in metal porcelain restorations, veneers and dental bridges, a foil having a color more similar to that of natural dentin in order to facilitate matching the complete restoration with the surrounding natural teeth. It would further be desirable to have a foil formed of a single alloy that is relatively easy to prepare. Furthermore, it would be desirable that the foil be heat resistant to minimize distortion when the overlaying porcelain is fired, yet sufficiently malleable to ensure proper fit of the foil to the die, and ultimately of the finished restoration to the mouth.

Such a metal foil could be fashioned into the metal substrate of a metal porcelain dental restoration or dental bridges, or the metal base of a metal porcelain dental veneer by use of conventional techniques or by the use of application of isostatic pressure as described in U.S.

Pat. No. 4,794,774, issued Jan. 3, 1989, the complete disclosure of which is incorporated herein by reference.

SUMMARY OF THE INVENTION

The present invention thus provides a metal foil for use as a substructure in a dental application. Specifically, the foil may be used in metal-porcelain dental restorations, dental bridges and in metal-porcelain dental veneers. The improved metal foil has superior color characteristics and superior bonding to porcelain compared with prior art foils. Metal-porcelain dental restorations made with the foil have improved aesthetic characteristics. Metal-porcelain dental veneers made with the foil are more aesthetically pleasing, especially because the use of the foil prevents any interference of the underlying tooth color or bonding material, is less expensive than such veneers made with cast metal, and are stronger and thinner than conventional all-ceramic veneers and thus occlusal and lingual as well as frontal and buccal veneers can be formed. Dental bridges that include copings made with the foil have aesthetic and strength advantages. Metal-porcelain dental bridges made with the metal and another layer of metal form unexpectedly strong joints between the teeth on either side of the edentulous region and the edentulous region itself.

The metal foil of the present invention also facilitates adhesion of the porcelain to the foil and has good heat resistance properties and good malleability.

The present invention overcomes the shortcomings of the prior art by providing a metal foil of an alloy comprising gold, an amount of platinum or palladium, and an amount of a non-precious metal. The platinum or palladium and the non-precious metal serve to adjust the color of the gold to an aesthetically pleasing color when used with porcelain in metal-porcelain dental restorations. The platinum or palladium is present in an amount sufficient to provide heat resistance to minimize distortion when the porcelain is baked, yet low enough to preserve the malleability of the gold. The non-precious metal promotes chemical bonding of the porcelain to the foil without the need of a bonding agent.

When used as an interior substructure for porcelain in a metal-porcelain dental restoration or dental bridge, the improved foil imparts superior color to the finished restoration, and superior bonding between the metal and porcelain. When used as a coping for the base of a dental bridge, the improved foil imparts superior color, fit, and strength to the bridge. When used in a dental bridge with a second layer of the same foil or of conventional foil, the joint strength is greatly enhanced.

When used as the base for porcelain in a metal porcelain dental veneer, the improved foil imparts superior color to the veneer, superior bonding between the metal and porcelain, and allows for a thinner, stronger veneer which can easily conceal even the most severe discoloration and can be used occlusally and lingually.

BRIEF DESCRIPTION OF THE DRAWINGS

For a more complete understanding of this invention, reference should now be made to the embodiment of the present invention illustrated in greater detail in the accompanying drawings.

FIG. 9 is a schematic lingual view of the pontic metal substructure after the application of the opaque layer.

FIG. 10 is a schematic lingual view of a completed dental bridge.

FIG. 11 is a schematic labial view of a completed dental bridge.

DETAILED DESCRIPTION

Figure 1:
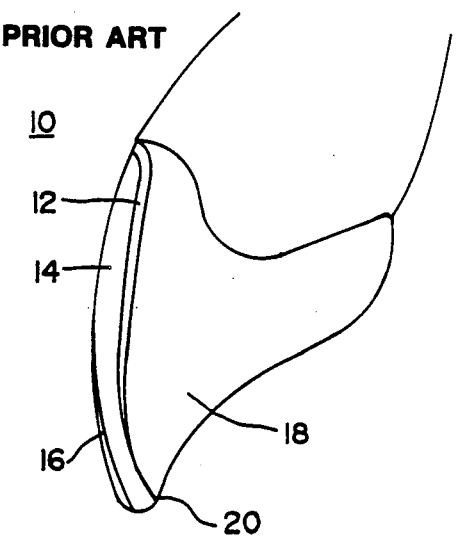
FIG. 1 is a schematic sectional view of a conventional veneer of the prior art.

The following detailed description is illustrative of the best mode presently known for carrying out the invention, and is not to be interpreted as limiting the disclosure.

In accordance with the invention, a metal foil which provides superior color, malleability, and chemical bonding to the porcelain, as well as improved heat resistance as compared with unalloyed gold is provided. The metal foil is formed of an alloy comprising at least about 88 wt % gold, platinum or palladium, and a non-precious metal.

As is known in the art, color is characterized by its hue, chroma, and value. Hue relates to the location of the color along the visible spectrum, that is, whether it is red, yellow, green, blue, brown, or so forth. Chroma, also known as saturation, relates to the intensity of the color, whether it is bright or pale. Value is the darkness or lightness of a color, and is a function of the amount of light reflected. In the present invention, the relative amounts of the alloy constituents are proportioned to obtain the desired balance of hue, chroma, and value for an aesthetically pleasing dental restoration.

As is known in the art, the reddish-orange color of pure gold foil is too red in hue as compared with the hue of the dentin of natural teeth. Also, the chroma of pure gold foil is undesirably high when compared with natural teeth. Adding a small amount of platinum alters the hue to a more acceptable yellowish shade closer to that of natural dentin. The platinum also reduces the chroma of the alloy. The platinum further imparts the advantages of improved heat resistance, whereby the foil will be less likely to become distorted during the porcelain firing process. It has been found that at least about 0.5 wt % platinum is desirable to achieve these advantages. It is also preferred that the proportion of platinum should not exceed about 7 wt %, in order to preserve the malleability of the foil when used with standard manipulation techniques. About 1–6 wt % platinum has been found satisfactory for most applications, and about 2–5 wt % platinum appears to give the best results. Palladium may be substituted for platinum with similar advantageous results, although care should be taken such that the palladium does not oxidize. Silver may also be substituted for the platinum. Silver has a lower melting point than gold and a much lower melting point than either platinum or palladium. The resulting alloy will therefore have a lower melting point, and will be suitable for use with porcelains having lower fusion temperatures.

The incorporation of a non-precious metal imparts several advantages to the foil. The non-precious metal reduces the amount of light reflected from the foil, thus adjusting the value of the foil closer to that of natural dentin. Additionally, during firing of the porcelain-metal restoration, wherein the porcelain paste is hardened, the non-precious metal at the surface of the foil will oxidize. The non-precious metal oxide also reacts with the porcelain, thereby promoting chemical bonding of the porcelain to the metal substructure, resulting in a metal-porcelain restoration of superior quality. At least about 0.1 wt % non-precious metal is necessary to achieve the advantages of the value adjustment and improved chemical bonding of the porcelain to the metal substructure. It has been found that at greater than about 5 wt % non-precious metal the foil becomes too dark, and the thermal resistance is also lessened. About 0.25-0.5 wt % non-precious metal has been found to be optimal for most applications. Suitable non-precious metals include indium, iron, zinc, aluminum, copper and like metals that readily form oxides, are nontoxic, and are otherwise able to withstand the chemical and physical environment of the human mouth.

Examples of alloys suitable for use in the instant invention are set forth in the following table. All numbers in the table indicate weight percent.

| Example | Gold | Platinum | Indium |
|---------|------|----------|--------|
| 1 | 97.75 | 2 | 0.25 |
| 2 | 97.5 | 2 | 0.5 |
| 3 | 97 | 2 | 1 |
| 4 | 95 | 2 | 3 |
| 5 | 94.75 | 5 | 0.25 |
| 6 | 94.5 | 5 | 0.5 |
| 7 | 94 | 5 | 1 |
| 8 | 92 | 5 | 3 |

The foil of the instant invention is prepared by first melting a desired quantity of gold, melting a predetermined amount of platinum, palladium or silver into the molten gold to obtain a molten alloy, and melting a predetermined quantity of a non-precious metal into the already molten alloy. Those skilled in the metallurgical arts will recognize the appropriate temperatures and conditions for preparing such a molten metal alloy. Further it will be understood that the molten alloy can be prepared in an air atmosphere, in a vacuum, or in an argon atmosphere, as may be required by the various metals and the proportions of each of the metal components. The molten alloy is then cooled. The alloy is then made into a foil by standard rolling techniques that increase the density of the material, thereby improving the strength of the foil. Satisfactory results may be obtained with a foil 25-200 microns thick. The preferred thickness range of 50-100 microns gives a foil that is sufficiently strong for this application yet thin enough to be easily workable.

As taught in the aforementioned U.S. Pat. No. 4,392,829, the finished foil may be sandblasted to provide a textured surface to which the porcelain will be applied. The textured surface provides microscopic sites for mechanical bonding of the porcelain to the foil. The foil may then be used to make a superior metal-porcelain dental restoration by standard methods or, for example, by the inventive method disclosed in U.S. Pat. No. 4,392,829 or the method disclosed in U.S. Pat. No. 4,794,774. The improved metal-porcelain restoration will allow greater ease in color matching.

As seen in FIG. 1, a conventional prior art dental veneer 10 consists of three layers of porcelain, an opacified dentin porcelain layer 12, a dentin porcelain layer 14 and an enamel porcelain layer 16. The total thickness of the three layer porcelain veneer 10 is generally greater than 500 microns. The layers are applied to the tooth 18 by first etching the surface 20 of the tooth 18. The veneer 20 is then bonded to the surface 20 of tooth 18 using a bonding agent. The conventional veneer 10 is formed in the laboratory and is subject to breakage whenever it is handled in the preparation, shipping, and application steps. Such conventional veneers do not posses good strength characteristics and thus are generally only used in frontal and buccal applications. Generally such conventional veneers are not used for occlusal or lingual veneers.

Figure 2:
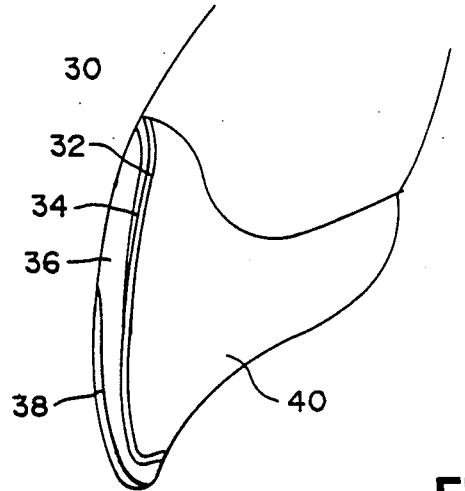
FIG. 2 is a schematic sectional side view of an anterior dental veneer of the present invention.
Figure 3:
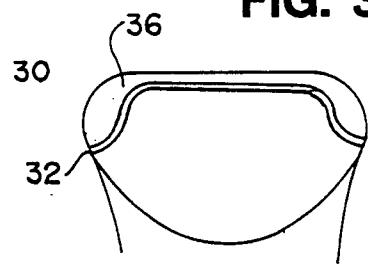
FIG. 3 is a schematic sectional top view of the anterior veneer of FIG. 2.

FIG. 2 shows an anterior veneer 30 made according to the present invention. The veneer 30 is made up of a layer 32 of metal which has baked thereon a layer 34 of opaque porcelain, a layer 36 of dentin porcelain and a layer 38 of enamel porcelain. FIG. 3 is a schematic top sectional view of the anterior veneer 30 of FIG. 2. The layer of metal 32 as well as layer 36 of dentin porcelain can be seen. The veneer 30, is bonded to tooth 40 as described below. Because metal layer 32 is completely opaque, the color of the bonding agent does not effect the color of the finished veneer.

In a preferred embodiment, the metal 32 is a metal foil of the composition previously set forth. More preferably, the layer 32 is such a metal foil which has been formed under isostatic pressure in a way similar to the method described in U.S. Pat. No. 4,794,774 and the surface of the foil is texturized as described in U.S. Pat. No. 4,392,829. Most preferably, the layer 32 is prepared as disclosed above and is approximately 50 microns thick. Preferably, the combination of the metal layer 32 and the opaque porcelain layer 34 is approximately 150 microns thick. The combination of the dentin porcelain layer 36 and the enamel porcelain layer 38 is preferably approximately 200 microns thick. Thus, the entire veneer 30 is less than 500 microns thick.

Even though veneer 30 is only 350 microns thick, the use of the improved metal foil as foil layer 32 results in a veneer 30 which is more natural in appearance than prior art veneers, is shadewise more controllable, covers all discoloration on the underlying tooth, and is stronger when compared to the prior art veneer.

Figure 4:
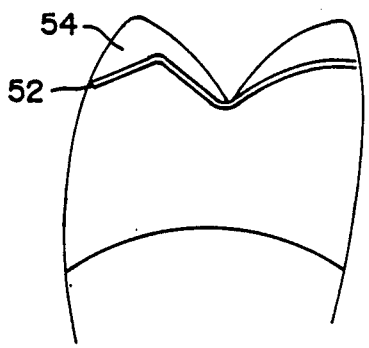
FIG. 4 is a schematic sectional view of a posterior occlusal veneer of the present invention.
Figure 5:
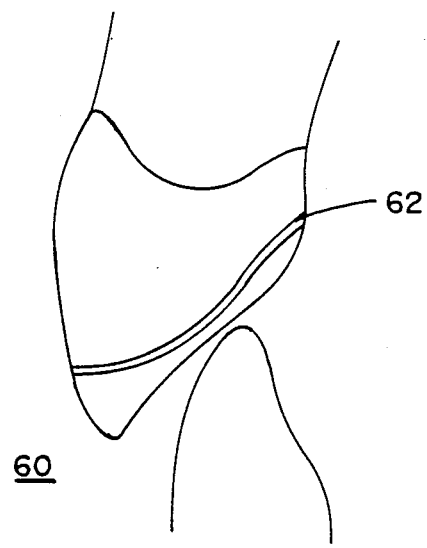
FIG. 5 is a schematic sectional view of a lingual veneer of the present invention.

Because of the strength of veneers made according to the present invention, it is possible to fabricate posterior occlusal veneers as seen in FIG. 4 and lingual veneers as seen in FIG. 5. A posterior occlusal veneer 50 is shown in FIG. 4 with a layer 52 of metal and a layer 54 of opaque porcelain. A lingual veneer 60 as in FIG. 5 is made from a layer 62 of metal and a layer 64 of opaque porcelain. The use of the metal as a base provides strength and the use of the particular metal of this invention allows the veneer to be aesthetically pleasing.

The veneers of the present invention are bonded to the underlying tooth using a bonding material. Before bonding, the surface of the tooth is etched to provide added adhesion. The preferred bonding material is a 4-Metacrylate resin sold under the trademark Superbond by Rocky Mountain Morita Co. and Certainbond by Rocky Mountain Orthodontics. After etching, the bonding agent comprising a monomer and catalyst is mixed and applied to the surface of the metal. Additional monomer is applied to the surface of the tooth, the veneer is seated and the bonding agent cures, creating a strong sure bond.

A porcelain dental restoration of the type referred to as a dental bridge is also advantageously formed of the metal foil of this invention as follows.

Figure 6:
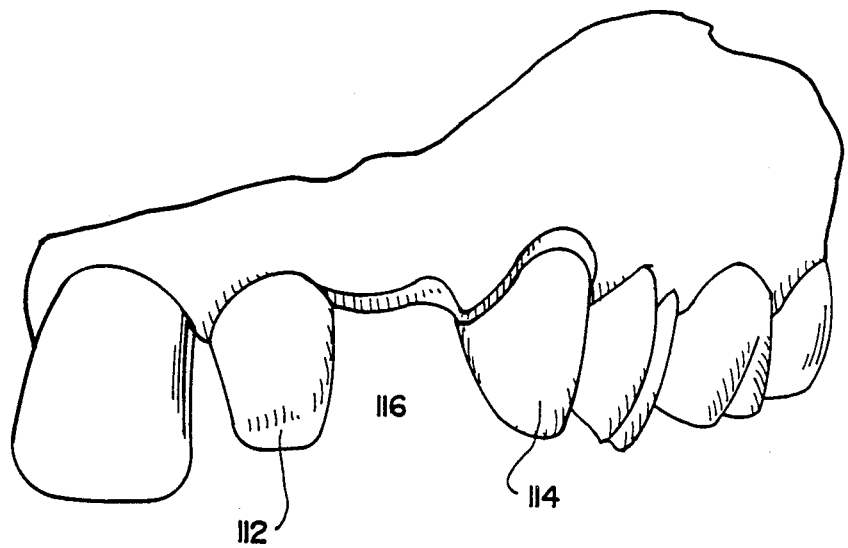
FIG. 6 is a schematic view of an edentulous region and the abutment teeth.

Referring to FIG. 6, the two abutment teeth 112 and 114 on either side of the edentulous region 116 are ground down to posts. Although the abutment teeth 112 and 114 will be generally smooth after grinding they will not be of uniform shape or configuration, and the dental bridge must be specially designed to fit the exact shape and configuration of the abutment teeth.

Figure 7:
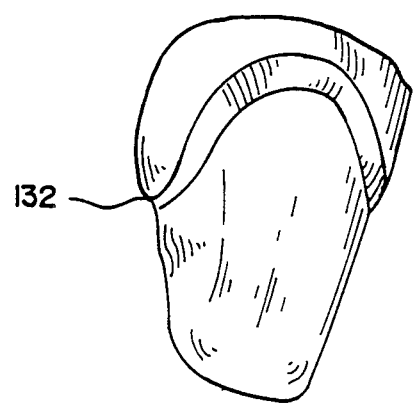
FIG. 7 is a schematic view of a coping for the abutment teeth.

As shown in FIG. 7, a metal foil coping 122 is formed for use on abutment tooth 112 (correspondingly, another coping, not shown, is formed for use on abutment tooth 114). This coping facilitates a close fit between the abutment teeth and the dental bridge by fitting exactly to the shape of the abutment teeth. The coping is made of the foil described above in order to provide an aesthetically pleasing margin or interface between the reconstruction and the adjacent gums. Moreover, it has been found that gingival tissue responds more favorably to the foil of this invention than to prior art foils. Preferably, the coping is made using the method disclosed in U.S. Pat. No. 4,794,774 in order to produce copings which are closely formed and has a good bond with the abutment teeth.

Figure 8:
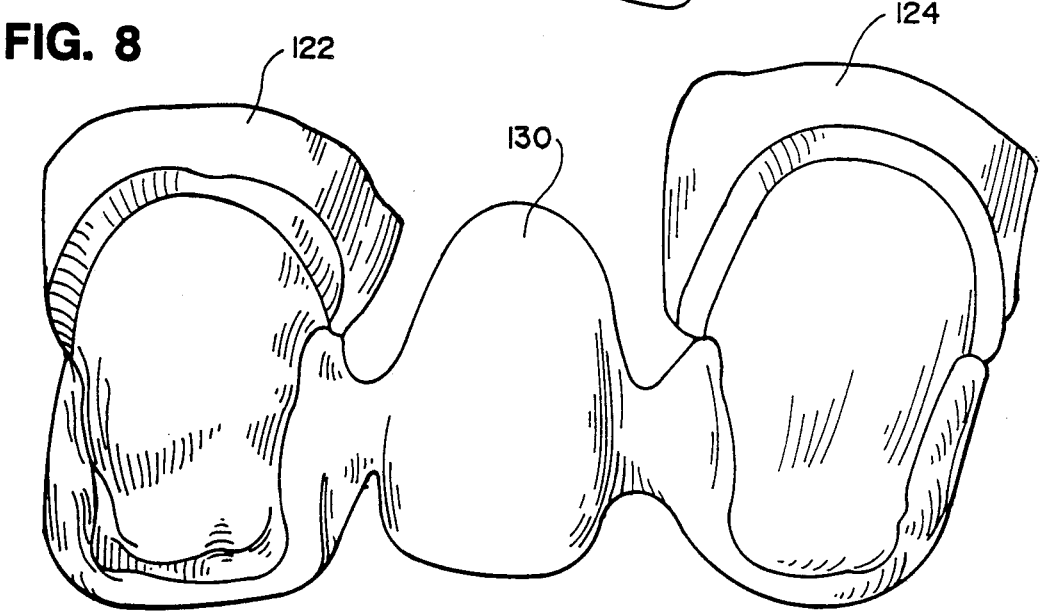
FIG. 8 is a schematic view of the pontic metal substructure affixed to the copings.

A metal pontic substructure 130, as shown in FIG. 8, is prepared by conventional lost wax technique. The copings 122 and 124 (for abutment teeth 112 and 114 respectively) are connected to the cast metal pontic substructure 130 with glue which will burn out when the opaque is baked. Consequently, a glue that will burn at a temperature less than the baking temperature of the opaque is required. Connections between the copings 122 and 124 and the metal pontic substructure 130 can also be accomplished by electric welding. Because the pontic substructure 130 is being connected to the copings 122 and 124 which can be made of a uniform shape, the connection is stronger than that used in the prior art where the substructure was connected directly to the abutment teeth without use of a coping. Thus, in the prior art, the pontic substructure had to be formed more carefully and still did not achieve the bonding strength of a bridge using copings formed from the improved metal foil.

As seen in FIG. 9 an opaque layer is then applied and the bridge 140 is built up using conventional ceramic method. After the opaque layer is applied, the glue is no longer necessary. The opaque layer holds the positions of the copings 122, 124 and the cast metal pontic substructure 130.

The opaque layer provides a base for the ceramic buildup comprising the reconstructions, as shown in FIGS. 10 and 11. Conventional methods can be used to reconstruct the abutment teeth 112 and 114 to obtain reconstructed teeth 142 and 144 respectively and to construct a tooth 146 in what used to be the edentulous region 116. As seen in FIG. 11, the metal copings 122 and 124 are visible between the reconstructed teeth 142 and 144 and the adjacent gums 150. While any dental foil can be used to make the copings use of the improved metal foil of this invention for the copings will provide an aesthetically pleasing interface or margin and allow the patient to smile normally without feeling self-conscious.

Figure 12:
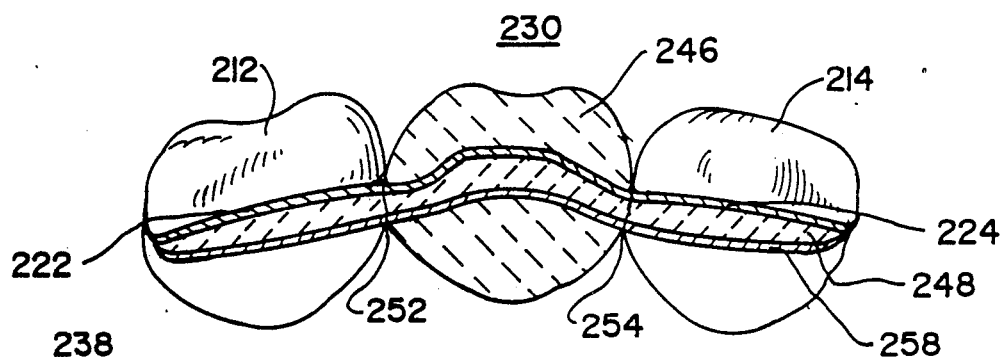
FIG. 12 is a schematic occlusal sectional view of a two-layer metal-porcelain dental bridge.
Figure 13:
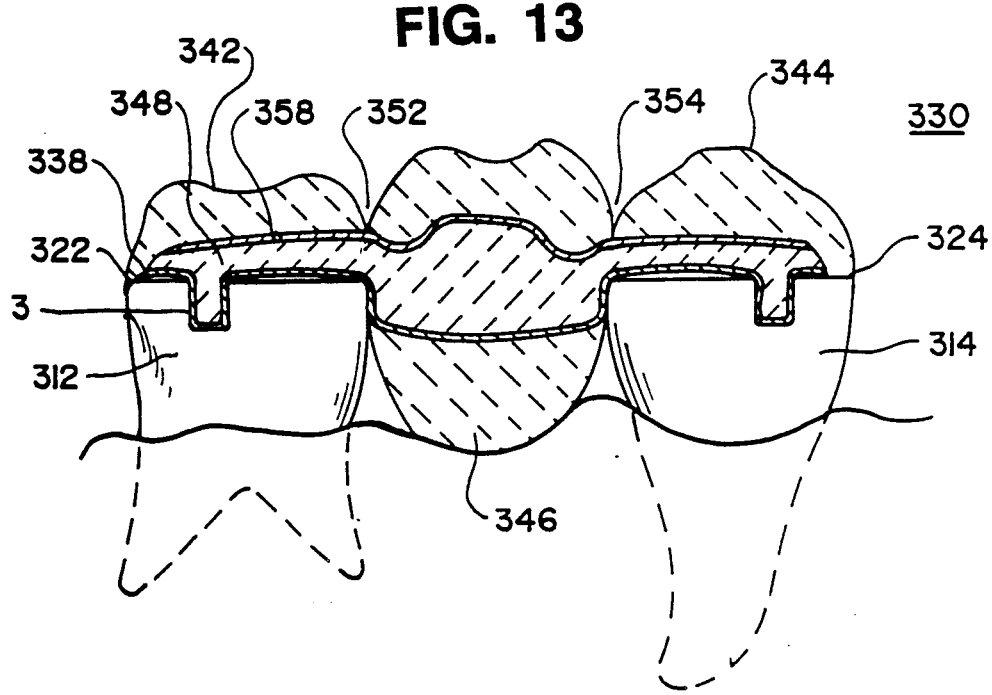
FIG. 13 is a schematic sectional view of a two-layer metal porcelain dental bridge.

Referring to FIGS. 12 and 13, a second embodiment of a dental bridge which uses the improved metal foil of the invention is disclosed. Rather than forming copings on the abutment teeth the metal foil of this invention can be advantageously used in a second manner to form a dental bridge.

Referring to FIG. 12, the two abutment teeth 212 and 214 are seen. Rather than grinding the abutment teeth to posts, only the lingual surface of abutment teeth 212 and 214 need to be ground, to produce generally flat bonding surfaces 222 and 224 respectively. A bridge 230 can then be formed by bonding a metal foil 238 to the generally flat surfaces 222 and 224 of abutment teeth 212 and 214. In order to get sufficient strength for the bridge, the bond between layer 238 and surfaces 222 and 224 must be tight and firm and the ceramic material must bond well to the foil. Thus, the improved metal of the present invention is used for metal foil layer 232 to provide the improved bonding characteristics as described above. This layer 238 is bonded to surfaces 222 and 224 as described above with respect to the bonding of dental veneers. The layer 238 extends through the edentulous region and forms the base for a traditional ceramic buildup to construct tooth 246 in the previously edentulous region.

It is known from prior art all ceramic bridges that the joint areas, the area between an abutment tooth and the previously edentulous region containing the ceramic restoration is particularly prone to breakage. Thus, as seen in FIG. 12, after an amount of ceramic material 248 is built up on metal foil layer 238 a second foil layer 258 is added. Generally, the ceramic material 248 between metal layers 238 and 258 would be from about 0.1 to about 0.3 millimeters thick. The second foil layer 258 can extend the entire length of the bridge as shown in FIG. 12 or could be used only in joint areas 252 and 254, extending only slightly past the joint areas. This second foil layer 258 can be the improved metal foil of this invention or it can be a conventional foil. The second foil layer does not have to be as malleable as the first layer because it does not have to fit as closely to the adjacent ceramic layers. Depending on the particular application, one of ordinary skill will know to choose the metal to advantageously enhance the strength characteristics of the bridge. One skilled in the art will recognize that if differing metals are used for layers 238 and 258 the expansion characteristics of the two metals and the ceramic must be matched so as not to unnecessarily stress and perhaps break the bridge 230 in manufacture or use.

FIG. 13 shows another two-layer bridge 330 of the present invention. This shows an application of the two-layer concept to a posterior bridge. In such a case, the abutment teeth 312 and 314 are ground down from the top to form surfaces 322 and 324. These surfaces may be substantially flat or, as shown, may contain notches 332 and 334 to impart added stability, strength and bonding. A layer 338 of the metal foil of this invention is bonded to surfaces 322 and 324. Again, an amount of ceramic material 348 as previously described is added and a second foil layer 358 is added. As described before this second layer 358 can extend throughout bridge 330 or can be located only around joints 352 and 354. Conventional methods are used to construct tooth 346 in the previously edentulous region and to reconstruct the occlusal surfaces of 342 and 344 of abutment teeth 312 and 314.

The use of the second foil layer 258 or 358 unexpectedly result in joints four times as strong as corresponding joints in a dental bridge made with only one layer of metal.

Obviously, many modifications and other embodiments of the subject invention will be recognized by one skilled in the art in view of the foregoing teachings. For example, while the disclosed alloy has been described as used in a foil substructure, it may also find utility as a cast substructure for dental restorations. Therefore, the invention is not to be limited thereto and any modifications are intended to be included within the scope of the appended claims.

What is claimed is:

1. A foil for use in a dental application, said foil comprising a three-component alloy consisting of a total of about 2–5 wt % of a color-adjusting metal from the group consisting of platinum, palladium, and silver; a total of about 0.1–5 wt % of a non-precious metal from the group consisting of indium, iron, zinc, aluminum, and copper; and the balance gold.

2. The foil of claim 1 wherein said non-precious metal comprises about 0.25–1 wt % of said foil.

3. The foil of claim 2 wherein said non-precious metal comprises about 0.25–0.5 wt % of said foil.

4. The foil of claim 3 wherein said non-precious metal comprises about 0.25 wt % of said foil.

5. The foil of claim 1 wherein said non-precious metal is indium.

6. The foil of claim 1 wherein said color-adjusting metal comprises about 3 wt % of said foil.

7. The foil of claim 1 wherein said color-adjusting metal is platinum.

8. The foil of claim 7 wherein said non-precious metal is indium.

9. The foil of claim 8 wherein said platinum comprises about 3 wt % of said foil and said indium comprises about 0.25 wt % of said foil.

10. A metal-porcelain dental restoration comprising:
    (a) an interior substructure of a thin metal foil of claim 1 having a textured exterior surface, and
    (b) a body porcelain layer bonded directly to the exterior of said substructure.

11. A metal-porcelain dental veneer comprising:
    (a) a thin metal foil of claim 1 for bonding to the tooth, and
    (b) a porcelain layer bonded to said foil.

* * * * *